US007564541B2

(12) United States Patent
Tuschel

(10) Patent No.: US 7,564,541 B2
(45) Date of Patent: Jul. 21, 2009

(54) SYSTEM FOR OBTAINING IMAGES IN BRIGHT FIELD AND CROSSED POLARIZATION MODES AND CHEMICAL IMAGES IN RAMAN, LUMINESCENCE AND ABSORPTION MODES

(76) Inventor: David Tuschel, 915 Harvard Rd., Monroeville, PA (US) 15146

( * ) Notice: Subject to any disclaimer, the term of this patent is extended or adjusted under 35 U.S.C. 154(b) by 158 days.

(21) Appl. No.: 11/393,395

(22) Filed: Mar. 30, 2006

(65) Prior Publication Data

US 2006/0170907 A1 Aug. 3, 2006

Related U.S. Application Data

(63) Continuation-in-part of application No. 11/252,414, filed on Oct. 18, 2005, and a continuation-in-part of application No. 10/882,088, filed on Jun. 30, 2004, and a continuation-in-part of application No. 10/879,636, filed on Jun. 30, 2004, now Pat. No. 7,408,636, application No. 11/393,395, which is a continuation-in-part of application No. 11/268,591, filed on Nov. 8, 2005, and a continuation-in-part of application No. 11/268,590, filed on Nov. 8, 2005.

(60) Provisional application No. 60/720,432, filed on Sep. 26, 2005, provisional application No. 60/625,014, filed on Nov. 3, 2004.

(51) Int. Cl.
G01N 21/00 (2006.01)
G01J 3/44 (2006.01)
(52) U.S. Cl. ........................ 356/73; 356/301; 356/417; 356/364; 356/445

(58) Field of Classification Search ............. 356/72–73, 356/301, 417, 364, 445
See application file for complete search history.

(56) References Cited

U.S. PATENT DOCUMENTS

| 6,825,921 | B1 * | 11/2004 | Modlin et al. | 356/73 |
| 2005/0012929 | A1 * | 1/2005 | Booker et al. | 356/73 |
| 2006/0051036 | A1 * | 3/2006 | Treado et al. | 385/117 |
| 2006/0250613 | A1 * | 11/2006 | Demuth et al. | 356/301 |
| 2006/0256330 | A1 * | 11/2006 | Leipertz | 356/73 |
| 2007/0081156 | A1 * | 4/2007 | Treado et al. | 356/301 |

* cited by examiner

Primary Examiner—Kara E Geisel
(74) Attorney, Agent, or Firm—Morgan Lewis & Bockius LLP

(57) ABSTRACT

An integrated system including one or more light sources, at least one processor, an optical lens, a two-dimensional tunable filter, one or more two-dimensional array of detection elements and instructions and a method using the integrated system. The system includes a plurality of modes: a Raman mode, an absorption mode, a luminescence mode, a crossed polarization mode, a crossed polarization absorption mode, bright field transmission or reflectance modes and a birefringence mode. The system includes instructions, executable by Sequential outputs from the two-dimensional array of detection elements is combined to generate a chemical image of the sample, wherein each of the sequential outputs from the first two-dimensional array of detection elements corresponds to spatially accurate wavelength-resolved images. The system is also used to detect dynamic changes in a sample over time by monitoring the sample using one or more of the modes.

15 Claims, 2 Drawing Sheets

SYSTEM FOR OBTAINING IMAGES IN BRIGHT FIELD AND CROSSED POLARIZATION MODES AND CHEMICAL IMAGES IN RAMAN, LUMINESCENCE AND ABSORPTION MODES

RELATED APPLICATIONS

This application is a continuation-in-part of U.S. patent application Ser. No. 10/879,636, filed Jun. 30, 2004, now U.S. Pat. No. 7,408,636 and a continuation-in-part of U.S. patent application Ser. No. 10/882,088, filed Jun. 30, 2004. This application is also a continuation-in-part of U.S. patent application Ser. No. 11/252,414 filed Oct. 18, 2005 which claims priority to U.S. provisional patent application No. 60/625,014 which was filed on Nov. 3, 2004. This application is a continuation-in-part of U.S. patent application Ser. No. 11/268,591, filed on Nov. 8, 2005 and U.S. patent application Ser. No. 11/268,590, filed Nov. 8, 2005 both of which claim priority of U.S. provisional patent application No. 60/720,432, filed Sep. 26, 2005. Each of the above referenced applications is incorporated herein by reference in its entirety. Each of the above referenced applications is assigned to the assignee of the present application.

FIELD OF DISCLOSURE

The present invention relates generally to a system to perform chemical imaging and to the use of chemical imaging to detect dynamic changes in a sample using a variety of detection modes.

BACKGROUND

Chemical imaging is known in the art. One example of an apparatus used for chemical imaging is taught in U.S. Pat. No. 6,002,476, entitled "Chemical Imaging System," to Treado et al. Another example of an apparatus used for chemical imaging is taught in U.S. Pat. No. 7,019,296, entitled "Near Infrared Chemical Imaging Microscope," to Treado et al.

In contrast to the prior art, the present disclosure describes a system to perform chemical imaging wherein a variety of detection modes are contained within a single system.

SUMMARY

The present disclosure provides a system and method that operate a variety of spectroscopic and microscopic detection modes. A substantially monochromatic light source illuminates a sample, along a first optical path, with a plurality of photons to thereby produce, along a second optical path, photons scattered or emitted from different locations on or within the sample wherein the first optical path is at an oblique angle with respect to the second optical path. A first white light source located under the sample illuminates the sample with broadband light to thereby produce, along the second optical path, photons transmitted through the sample; and a second white light source located above the sample that illuminates the sample with broadband light to thereby produce, along the second optical path, photons reflected from different locations on or within the sample. At least one processor generates first control signals that control operation of the substantially monochromatic light source, the first white light source and the second white light source. An optical lens, positioned in the second optical path, collects photons scattered, emitted, or transmitted along the second optical path. A two-dimensional tunable filter, responsive to second control signals generated by the at least one processor and positioned in the second optical path, sequentially passes photons, in each of a plurality of predetermined wavelength bands, which were scattered or emitted from different locations on or within the sample or transmitted through the sample. A first two-dimensional array of detection elements, responsive to third control signals generated by the at least one processor, detects in a spatially accurate manner photons passed by the two-dimensional filter which were scattered or emitted from different locations on or within the sample or transmitted through the sample. A second two-dimensional array of detection elements, responsive to fourth control signals generated by the at least one processor, detects in a spatially accurate manner photons reflected from different locations on or within the sample and generates an image.

The system includes instructions, executable by the at least one processor, for alternatively configuring the system in a Raman mode, a luminescence mode, an absorption mode and bright field transmission or reflection modes. In the Raman mode, the first control signals control operation of the substantially monochromatic light source in order to produce photons scattered from different locations on or within the sample, the second control signals control operation of the two-dimensional tunable filter such that the tunable filter sequentially passes photons, in each of a plurality of predetermined wavelength bands, which were scattered from different locations on or within the sample, and the third control signals control operation of the first two-dimensional array of detection elements in order to detect in a spatially accurate manner photons passed by the two-dimensional filter which were scattered from different locations on or within the sample. In the luminescence mode, the first control signals control operation of the substantially monochromatic light source in order to produce photons emitted from different locations on or within the sample, the second control signals control operation of the two-dimensional tunable filter such that the tunable filter sequentially passes photons, in each of a plurality of predetermined wavelength bands, which were emitted from different locations on or within the sample, and the third control signals control operation of the first two-dimensional array of detection elements in order to detect in a spatially accurate manner photons passed by the two-dimensional filter which were emitted from different locations on or within the sample. In the absorption mode, the first control signals control operation of the first white light source in order to produce photons transmitted through the sample, the second control signals control operation of the two-dimensional tunable filter such that the tunable filter sequentially passes photons, in each of a plurality of predetermined wavelength bands, which were transmitted through the sample, and the third control signals control operation of the first two-dimensional array of detection elements in order to detect in a spatially accurate manner photons passed by the two-dimensional filter which were transmitted through the sample. In the bright field modes, the first control signals control operation of one of the following: the first and the second white light source in order to produce photons transmitted or reflected from different locations on or within the sample, respectively, and the fourth control signals control operation of the second two-dimensional array of detection elements in order to detect in a spatially accurate manner photons which were transmitted or reflected from different locations on or within the sample and to generate a bright field transmission or reflectance image.

The at least one processor combines sequential outputs from the first two-dimensional array of detection elements to generate a chemical image of the sample, wherein each of the sequential outputs from the first two-dimensional array of detection elements corresponds to spatially resolved photons in one of the plurality of predetermined wavelength bands passed by the two-dimensional tunable filter and detected by the first two-dimensional array of detection elements.

In one embodiment, the system and method may also include a first polarizing filter located between the white light source and the sample; and a second polarizing filter located between the sample and the tunable filter, that receives one of transmitted or reflected photons, and is oriented 90° with respect to the first polarizing filter. In yet another embodiment, the system may include a compensator located above the sample.

In yet another embodiment, the processor analyzes the outputs from the first two-dimensional array of detection elements or the second two-dimensional array of detection elements, using one or more aspects of the sample that identify the sample. The one or more aspects of the sample comprise wavelength, frequency, phase, polarization, an intensity of wavelength, an intensity of frequency, or combinations thereof.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DETAILED DESCRIPTION OF THE DISCLOSURE

Figure 1:
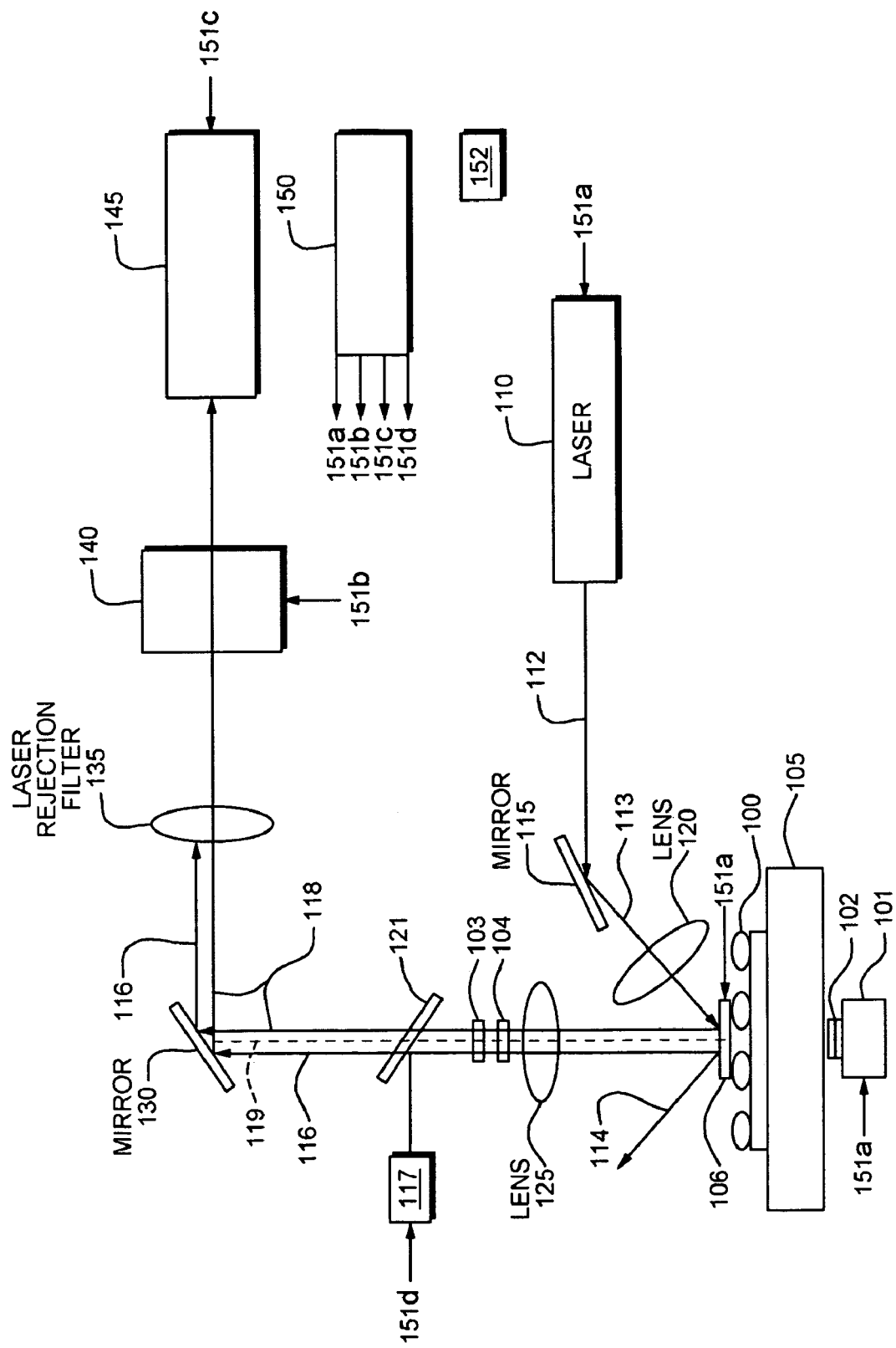
FIG. 1 schematically represents an apparatus according to one embodiment of the disclosure.

FIG. 1 schematically represents a system according to one embodiment of the disclosure. The system of FIG. 1 provides a high optical throughput for imaging low light levels at variable magnification. The system of FIG. 1 operates in a plurality of modes including a Raman mode, an absorbtion mode, a luminescence mode, a crossed polarization mode, a crossed polarization absorption mode, bright field transmission or reflectance modes, and a birefringence mode.

Referring to FIG. 1, sample 100 is positioned on substrate 105. Substrate 105 can be any conventional microscopic slide, a hot stage, a microfluidic circuit, or other means for receiving and optionally securing sample 100. The use of a microfluidic circuit in chemical imaging applications is disclosed in U.S. patent application Ser. No. 10/920,320, filed on Aug. 18, 2004, entitled "Method and Apparatus for Chemical Imaging in a Microfluidic Circuit" which is incorporated herein in its entirety. A substantially monochromatic light source 110 is positioned to provide incident light to sample 100. Light source 110 can include any conventional photon source, including laser, LED, and other IR or near IR devices. Light source 110 may also be selected to provide evanescence illumination of the sample. In one embodiment, the line width of the monochromatic light source is in the range of about 15-25 cm$^{-1}$.

Referring still to FIG. 1, it should be noted that the monochromatic light source 110 is positioned to provide incident light along a first optical path 113, which is at an angle to sample 100 as opposed to light shining orthogonal to sample 100. In other words, the radiation used to illuminate the sample need not pass through the optical train of a conventional microscope (or macroscope); rather, it can illuminate the sample at an oblique angle from above or below sample 100. Photon beam 112 is received and deflected by mirror 115 through lens 120. Lens 120 may optionally be used to focus the light on sample 100. Alternatively, the photon beam 112 may be directed towards the sample 100 without the need for the mirror 115.

The multitude of photons in beam 112 reaching sample 100 illuminate the sample and are either scattered or absorbed from different locations on or within the sample, which can result in subsequent emission (luminescence) at different wavelengths. As known to those skilled in the art, the term "luminescence" includes a wide range of optical processes described using other names. These include: fluorescence, phosphorescence, photoluminescence, electroluminescence, chemiluminescence, sonoluminescence, thermoluminescence and even upconversion. Scattered photons are schematically represented as beam 116 while specularly reflected photons are represented schematically as beam 114. Luminescence emitted photons are represented as beam 118. The scattered and emitted photons are produced along a second optical path 119, wherein the first optical path 113 is at an oblique angle with respect to the second optical path 119.

With further reference to FIG. 1, the apparatus of the present disclosure includes a first white light source 101 and a second white light source 106. The first white light source 101 is located under the sample 100. The second white light source 106 is located above the sample 100. The first white light source 101 and the second white light source 106 may include any light source which produces broadband light.

The photons from the first white light source 101 illuminate the sample 100 and are either absorbed or reflected by the sample or transmitted through the sample. Transmitted photons are schematically represented as beam 118. The photons from the second white light source 106 illuminate the sample and are either absorbed by the sample 100 or transmitted through the sample 100 or reflected from different locations on or within the sample 100. Reflected photons from the sample 100 are schematically represented also as beam 118. The transmitted photons from the sample are produced along a second optical path 119.

When the apparatus illustrated in FIG. 1 operates in a crossed polarization mode, the apparatus includes a first polarizing filter 102 located between the first white light source 101 and the sample 100 and a second polarizing filter 103 located above the sample 100 and before the tunable filter 140. The first polarizing filter 102 receives light from the first white light source 101 and transmits linearly polarized light to the sample 100. The second polarizing filter 103 receives transmitted photons and determines the plane of vibration for the polarized light. The second polarizing filter 103 is oriented 90° with respect to the first polarizing filter 102. When the apparatus operates in a birefringence mode, the apparatus further includes a compensator 104 located above the sample 100 and before the second polarizing filter 103. Transmitted photons are passed through the compensator 104.

Optical lens 125 is positioned along the second optical path 119 to collect photons scattered, emitted or transmitted, represented by photon beams 116 and 118. Optical lens 125 may be used for gathering and focusing received photon beams. This includes gathering and focusing both polarized and the un-polarized photons. In general, the sample size determines the choice of light gathering optical lens 125. For example, a microscope lens may be employed for analysis of the sub-micron to micrometer specimens. For larger samples, macro lenses can be used. Optical lens 125 (as well as lens 120) may include a simple reduced resolution/aberration lens with a larger numerical aperture to thereby increase the system's optical throughput and efficiency. Mirror 130 is positioned to direct emitted, scattered, or transmitted photon beams, 116 and 118, respectively, to tunable filter 140. It should be noted that placement of mirror 130 is optional and may be unnecessary in configurations where the tunable filter is positioned above sample 100.

Laser rejection filter 135 may be positioned prior to tunable filter 140 to filter out elastic scattered illumination light represented by beam 116 and to optimize the performance of the system. In other words, rejection filter 135 enables spectral filtering of the photons at the illuminating wavelength.

A two-dimensional tunable filter 140, including electro-optical tunable filters, liquid crystal tunable filter ("LCTF") or acousto-optical tunable filter ("AOTF"), can be used to further the principles of the disclosure. The tunable filter 140 is positioned in the second optical path 119. The electro-optical filter (interchangeably, tunable filters) sequentially passes the scattered, emitted or transmitted photons in each of a plurality of predetermined wavelength bands. The plurality of predetermined wavelength bands include specific wavelengths or ranges of wavelengths. In one embodiment, the predetermined wavelength bands include wavelengths characteristic of the sample undergoing analysis. The tunable filter 140 is responsive to second control signals, generated by the processor 145, wherein the second control signals establish the predetermined wavelength bands. The wavelengths that can be passed through tunable filter 140 may range from 200 nm (ultraviolet) to 2000 nm (i.e., the far infrared). The choice of tunable filter depends on the desired optical region and/or the nature of the sample being analyzed. The two-dimensional tunable filter includes a Fabry Perot angle tuned filter, an acousto-optic tunable filter, a liquid crystal tunable filter, a Lyot filter, an Evans split element liquid crystal tunable filter, a Solc liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, and a liquid crystal Fabry Perot tunable filter. The tunable filer is selected to operate in one or more of the following spectral ranges: the ultraviolet (UV), visible, near infrared, and mid-infrared.

The first two-dimensional array of detection elements 145 ("first detector") may include a digital device such as for example an image focal plane array ("FPA") or CCD or CMOS sensor. The optical region employed to characterize the sample of interest governs the choice of two-dimensional array detector. For example, a two-dimensional array of silicon charge-coupled device ("CCD") detection elements can be employed with visible wavelength fluorescence and Raman spectroscopic, while gallium arsenide (GaAs) and gallium indium arsenide (GaInAs) FPA detectors can be employed for image analyses at near infrared wavelengths. The choice of such devices depends on the type of sample being analyzed. The first detector 145 detects, in a spatially accurate manner, the scattered, emitted or transmitted photons passed by the tunable filter 140. The first detector 145 is responsive to third control signals generated by the processor 150. In one embodiment, each detection element in the first two-dimensional array of detection elements used to form the detection array 145 functions to detect photons scattered, or emitted from a different spatial location on or within the sample or transmitted photons from the sample. In one embodiment, the two-dimensional array of detection elements 145 produces digital images of the entire view of the sample as processed by tunable filter 140.

The second two-dimensional array of detection elements 117 ("second detector") may include a digital device such as for example CCD or CMOS sensor to detect reflected photons. The second two-dimensional array of detection elements 117 is responsive to fourth control signals 151d generated by the processor 150 to generate an image. In one embodiment, the second detector generates bright field transmission or reflectance images. In another embodiment, the second detector generates a crossed polarization image. In yet another embodiment, the second detector generates a birefringence image. The system also includes element 121.

Figure 2:
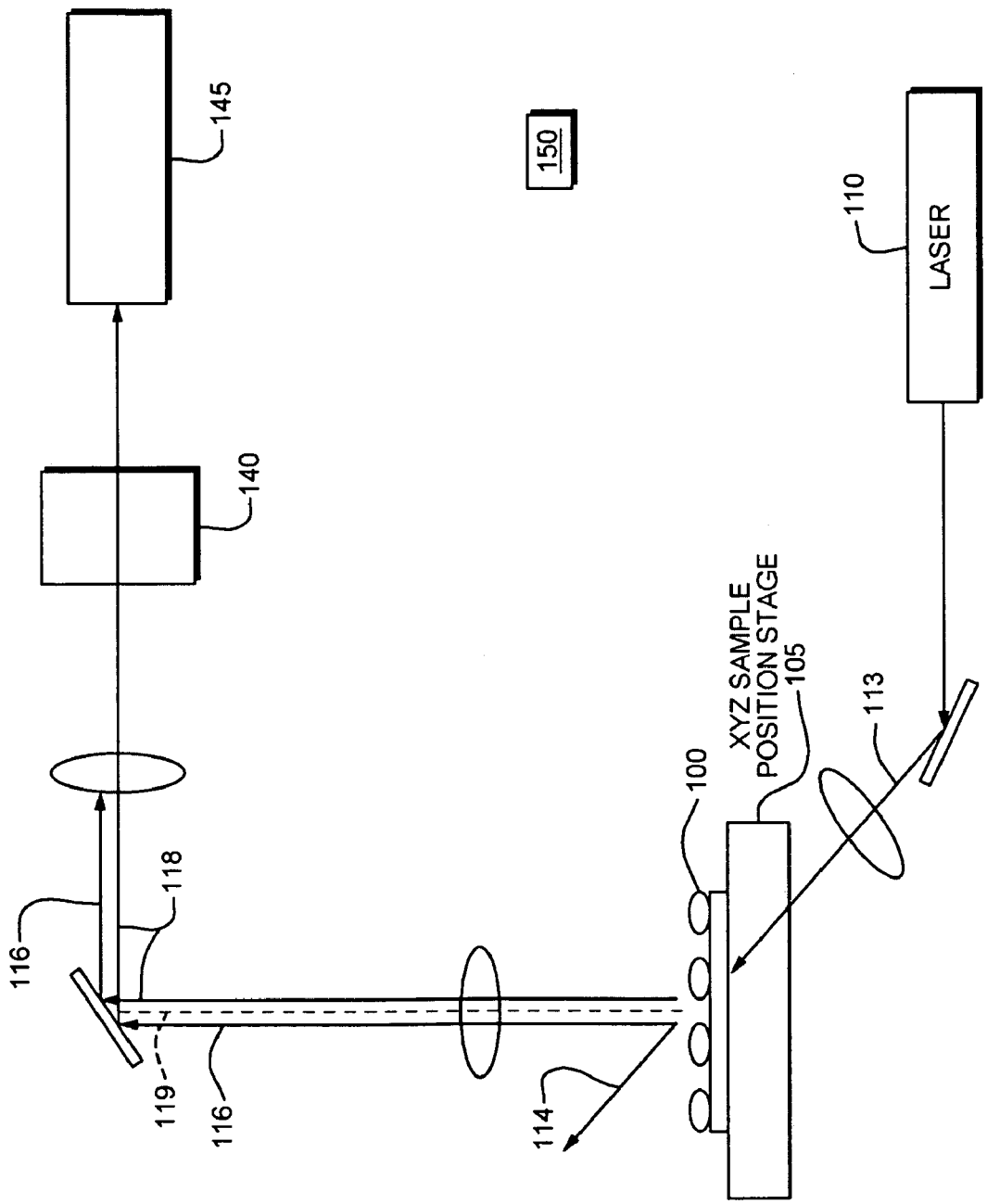
FIG. 2 schematically represents an apparatus according to another embodiment of the disclosure.

FIG. 2 schematically represents a system according to another embodiment of the disclosure. More specifically, FIG. 2 schematically shows a high optical throughput configuration for imaging low light levels at variable magnification. The collection of optics is similar to that illustrated in FIG. 1 but with illumination from the underside of sample 100.

It is noted that in both FIGS. 1 and 2, sample 100 is illuminated at an oblique angle. Specifically referring to FIG. 2, photon beam 113 and the plane axis of sample 100 define an oblique angle. It has been found that through oblique illumination, a so-called "Dark Field Raman Imaging" is developed. As opposed to the conventional bright field Raman configuration, the dark field Raman imaging decouples the image capture optics from the delivery of exciting radiation. Consequently, internal scattering and attenuation of the incident radiation has been minimized to improve the signal to noise ratio. Also, the location of the optical source external to the optical train further allows the use of a lower cost, less powerful illumination source as well as enables a simpler, less expensive integration of several illumination sources into the system. In addition, it allows for coupling of the illumination beam into devices such as waveguides, integrated optics and microfluidic devices. The application of this configuration is not limited to Raman and luminescence imaging and can be successfully used, for example, with conventional spectroscopy.

In each of the embodiments shown in FIGS. 1 and 2, at least one processor 150 is coupled to and used to control the optical devices of the apparatus illustrated in FIGS. 1 and 2, including lenses 120, 125, 135 and mirrors 115, 130. Processor 150 generates first control signals 151a to control the substantially monochromatic light source 110, the first and second white light sources 101 and 106. Second control signals 151b, generated by processor 150, control the tunable filter 140. Processor 150 is coupled to the first two-dimensional array of detection elements 145 which is responsive to third control signals 151c generated by the processor 150. Based on the third control signals 151c, first detector 145 generates output in the form of "chemical images." In one embodiment, each chemical image is a spatially accurate wavelength-resolved image of the sample that is formed from multiple "frames"; wherein each frame has plural spatial dimensions and is created from photons of a particular wavelength (or wave number) or from photons in a particular wavelength band (or wave number band) that are collected simultaneously by first detector 145 from different spatial locations on or within sample 100. In each chemical image, multiple frames may be combined to form a complete image across all wavelengths (wave numbers) of interest. The chemical images generated by the processor 150 may be further analyzed by the processor and/ or displayed to a user. Processor 150 is also coupled to the second two-dimensional array of detection elements 117 which is responsive to fourth control signals 151d generated by processor 150. Based on the fourth control signals 151d, the second detector 117 generates an image. The image includes bright field transmission or reflectance images, a crossed polarization image, and a birefringence image.

The system further includes instructions 152, executable by processor 150, for alternatively configuring the system in a Raman mode, a luminescence mode, an absorption mode, bright field transmission or reflection modes, crossed polarization mode, a crossed polarization absorption mode and a birefringence mode. In the Raman mode, the processor 150 executes instructions 152 wherein the first control signals control operation of the substantially monochromatic light source 110 in order to produce photons scattered from different locations on or within the sample 100. The second control signals control operation of the two-dimensional tunable filter 140 such that the tunable filter 140 sequentially passes photons, in each of a plurality of predetermined wavelength bands, which were scattered from different locations on or within the sample 100. The third control signals control operation of the first two-dimensional array of detection elements 145 in order to detect in a spatially accurate manner photons passed by the two-dimensional filter 140 which were scattered from different locations on or within the sample 100.

In the luminescence mode, the processor 150 executes instructions 152 wherein the first control signals control operation of the substantially monochromatic light source 110 in order to produce photons emitted from different locations on or within the sample 100. The second control signals control operation of the two-dimensional tunable filter 140 such that the tunable filter 140 sequentially passes photons, in each of a plurality of predetermined wavelength bands, which were emitted from different locations on or within the sample 100. The third control signals control operation of the first two-dimensional array of detection elements 145 in order to detect in a spatially accurate manner photons passed by the two-dimensional filter 140 which were emitted from different locations on or within the sample 100.

In the absorption mode, the processor 150 executes instructions 152 wherein the first control signals control operation of the first white light source 101 in order to produce photons transmitted through the sample. The second control signals control operation of the two-dimensional tunable filter 140 such that the tunable filter 140 sequentially passes photons, in each of a plurality of predetermined wavelength bands, which were transmitted through the sample 100. The third control signals control operation of the first two-dimensional array of detection elements 145 in order to detect in a spatially accurate manner photons passed by the two-dimensional filter 140 which were transmitted through the sample 100.

In the bright field transmission or reflectance modes, the processor 150 executes instructions 152 wherein the first control signals control operation of one of the following: the first white light source 101 and the second white light source 106 in order to produce photons transmitted or reflected from different locations on or within the sample 100, respectively. The fourth control signals control operation of the second two-dimensional array of detection elements 117 in order to detect in a spatially accurate manner photons which were transmitted or reflected from different locations on or within the sample 100 and to generate bright field transmission or reflectance images.

Processor 150 combines sequential outputs from the first two-dimensional array of detection elements 145 to generate a chemical image of the sample, wherein each of the sequential outputs from the first two-dimensional array of detection elements 145 corresponds to spatially resolved photons in one of the plurality of predetermined wavelength bands passed by the two-dimensional tunable filter 140 and detected by the first two-dimensional array of detection elements 145.

In the crossed polarization mode, the processor 150 executes instructions 152 wherein the first control signals control operation of the first white light source in order to produce photons transmitted from different locations on or within the sample 100. The fourth control signals control operation of the second two-dimensional array of detection elements 117 in order to detect in a spatially accurate manner photons which were transmitted from different locations on or within the sample 100 and to generate a crossed polarization image.

In the crossed polarization absorption mode, the processor 145 executes instructions 152 wherein, the first control signals control operation of the first white light source 101 in order to produce photons transmitted through the sample 100. The second control signals control operation of the two-dimensional tunable filter 140 such that the tunable filter 140 sequentially passes photons, in each of a plurality of predetermined wavelength bands, which were transmitted from different locations on or within the sample 100. The third control signals control operation of the first two-dimensional array of detection elements 145 in order to detect in a spatially accurate manner photons passed by the two-dimensional filter 140 which were transmitted through the sample 100.

In the birefringence mode, the processor 150 executes instructions 152 wherein the first control signals control operation of the first white light source 101 in order to produce photons transmitted from different locations on or within the sample 100. The fourth control signals control operation of the second two-dimensional array of detection elements 117 in order to detect in a spatially accurate manner photons which were transmitted from different locations on or within the sample 100 and to generate a birefringence image.

The present disclosure provides for a method performed using in an integrated system that includes one or more light sources 101, 106 and 110, at least one processor 150, an optical lens 125, a two-dimensional tunable filter 140, one or more two-dimensional array of detection elements 117, 145 and instructions. A sample 100 is illuminated, using a substantially monochromatic light source 110, along a first optical path 113, with a plurality of photons to thereby produce, along a second optical path 119, photons scattered or emitted from different locations on or within the sample 100 wherein the first optical path 113 is at an oblique angle with respect to the second optical path 119. The sample 100 is illuminated using at least one of the following: a first white light source 101, located under the sample 100 that illuminates the sample 100 with broadband light to thereby produce, along the second optical path 119, photons transmitted through the sample 100 or a second white light source 106, located above the sample 100 that illuminates the sample 100 with broadband light to thereby produce, along the second optical path 119, photons reflected from different locations on or within the sample 100. The at least one processor 150 generates first control signals that control operation of the substantially monochromatic light source 110, the first white light source 101 and the second white light source 106. The optical lens 125, positioned in the second optical path 119, collects ones of photons scattered, emitted or transmitted along the second optical path 119. The two-dimensional tunable filter 140, sequentially passes ones of photons, in each of a plurality of predetermined wavelength bands, which were scattered or emitted from different locations on or within the sample 100 or transmitted through the sample 100, wherein the two-dimensional tunable filter 140 is responsive to second control signals generated by the at least one processor 150 and positioned in the second optical path 119. A first two-dimensional array of detection elements detects 145, in a spatially accurate manner, ones of photons passed by the two-dimensional filter 140 which were scattered or emitted from different locations on or within the sample 100 or transmitted through the sample 100, wherein the first two-dimensional array of detection elements 145 responsive to third control signals generated by the at least one processor 150. The second two-dimensional array of detection elements 117 optionally detects, in a spatially accurate manner, ones of photons reflected from different locations on or within the sample 100, wherein the second two-dimensional array of detection elements 117 is responsive to fourth control signals generated by the at least one processor 150 and generates an image.

Instructions 152 are executed by the processor 150 for alternatively configuring the system in a Raman mode, a luminescence mode, an absorption mode and a bright field transmission or reflection mode, a crossed polarization mode, a crossed polarization absorption mode and a birefringence mode. Processor 150 then combines sequential outputs from the first two-dimensional array of detection elements 150 to generate a chemical image of the sample 100, wherein each of the sequential outputs from the first two-dimensional array of detection elements 145 corresponds to spatially resolved photons in one of the plurality of predetermined wavelength bands passed by the two-dimensional tunable filter 140 and detected by the first two-dimensional array of detection elements 145.

In yet another embodiment, the outputs, from the first two-dimensional array of detection elements 145 or the second two-dimensional array of detection elements 117, are analyzed by the processor 150. One or more aspects of the sample 100 that identify the sample 100 are used in the analysis. The aspect of the output, which the processor analyzes, may include wavelength, frequency, phase, polarization, an intensity of the wavelength or frequency, or combinations thereof. The output includes spatially resolved photons in one of the plurality of predetermined wavelength bands passed by the two-dimensional tunable filter 140 and detected by the first two-dimensional array detector 150. For scattered photons, this output includes a plurality of spatially resolved Raman spectra, a plurality of spatially resolved luminescence spectra or a combination thereof. For transmitted photons, this output includes a plurality of spatially resolved near infrared spectra, a plurality of spatially resolved visible spectra, a plurality of spatially resolved ultraviolet spectrum and combinations thereof. The output may also include a combination of more than one of the following: a plurality of spatially resolved Raman spectra, luminescence spectra, near infrared spectra, visible spectra, ultraviolet spectra or combinations thereof. The sample, undergoing analysis, may include a cell, a drug, a metabolite of the drug, a compound bound to a constituent of a cell, a compound covalently bonded to a constituent of a cell.

The system and method of the present disclosure permit the spectroscopic and microscopic characterization of a sample while operating in plurality of spectroscopic and microscopic modes. In general, spectroscopic analysis of chemical systems can yield information that reflects the occurrence of particular chemical sample present in the chemical system. Chemical imaging can further indicate the physical location of the sample in the system, physical or chemical information (e.g., crystalline state of the sample and information about the environment in which the sample occurs), and information about the amount or concentration of the sample in the system or at particular locations therein.

The system and method of the present disclosure may be used in a variety of applications including bio-imaging of cells and cellular constituents, drug degradation, analyte-cell interaction, polymorph identification of crystalline compounds, chemical particle sizing, crystallinity, morphology, birefringence or combinations of thereof.

The system and method described herein are suitable for bio-imaging of cells of substantially any type, and constituents of a cell. The cell includes one or more cells of any eukaryote or prokaryote or mixed samples of the two or more cell types. Exemplary cells include cells of humans, non-human animals, agriculturally significant plants (e.g., crop plants and weeds) or other plants, fungi, protists, eubacteria, archaebacteria, and mycoplasmas. Exemplary constituents of cells include a protein, an organelle, a protein complex, a compartment, and a membrane. Cells analyzed using these methods can be obtained from a sample and imaged at a remote location, optionally after maintaining the cells in culture, treating the cells with a fixative, treating the cells with a drug, freezing the cells, or some combination of these. Alternatively, when the location of the cells and the design of the equipment described herein are compatible, the cells can be imaged in situ, for example in a human tissue, on the surface of an object, or within a three-dimensional body that permits Raman spectral analysis of at least a part of its interior.

In yet another embodiment, the system and method of this disclosure may be used to analyze analyte-cell interactions. The analyte may include a drug, a molecule having a fluorophore, a metabolite of the drug or combinations thereof. For example, when an analyte such as a drug binds with a cell or a cellular component, some of the spectroscopic aspects which identify the drug compound will often shift reflecting the interactions and bonding of the drug within the cell. For analysis of an analyte within a cell, the system of FIGS. 1 and 2 includes magnification optics that permits visualization of cells or sub-cellular structures. One of skill in the art will understand that the selection of magnification optics will depend on the degree of detail needed in the analysis, the size of the sample or the desired resolution of portions of the sample. To analyze the analyte-cell interaction, an image frame of spectroscopic data is obtained for a desired sample, such as a cell or a portion of a cell, at one or more spectroscopic aspects that identify the analyte. Changes in the spectroscopic aspect(s) are then monitored. Spectral effects that reveal chemical interactions are changes in band intensity, shifts in band position, and changes in band width or band shape or symmetry. These and other effects will be monitored.

In one embodiment, the analyte includes a Raman-active drug molecule or a Raman-active molecule of cellular origin that is known or expected to be influenced by a drug molecule. Occurrence, approximate concentration or amount, and location of the Raman-active component can be assessed in the focal plane of the field of view. The Raman spectral data can be combined with (e.g., overlaid with) a frame of image data obtained by another analytical mode including bright field and crossed polarization modes. The Raman spectral data can be combined with other spectroscopic modes including luminescence and absorption modes.

In one embodiment, the analyte is a two component system wherein one component produces scattered photons and the other component emits photons upon illumination. Using the system of FIGS. 1 and 2, Raman images are obtained at wavelengths or frequencies, that identify the component which produces scattered photon. Luminescence images are obtained, at wavelengths or frequencies that identify the component which emitted photons. The Raman and luminescence images are then used to analyze the cell-analyte interaction. Spectral effects that reveal chemical interactions are changes in band intensity, shifts in band position, and changes in band width or band shape or symmetry. These and other effects will be monitored in both the Raman and luminescence images.

The system and method of the present disclosure may be used for spectroscopy analysis of the volume of an individual cell or throughout a three-dimensional mass of cells. In one embodiment, the method further includes the step of generating control signals that control the focusing depth of a lens and repeatedly performing the steps of passing, detecting, analyzing at different focusing depths. The outputs, at the different focusing depths are then combined to produce a three-dimensional image of the cell volume or volume of the mass of cells. In one embodiment, the sample includes a single cell, which is analyzed by repeatedly using different focusing depths within the cell to provide planar sections of such projections of the Raman chemical image throughout the volume of the cell. These chemical sections show subtle variations which can be assembled and processed to obtain three dimensional images of the drugs in cells. Such volumetric imaging depends on accurately achieving clear and accurate chemical images of the drug for each 'chemical' section (i.e., each focal plane), which is essential for such full volumetric imaging. Thus obtaining accurate chemical images for a single layer, section or two-dimensional projection of the cell as it lies on a substrate is important for volumetric imaging.

The system of FIGS. 1 and 2 and described herein can collect spectroscopic and image data over an entire field of view very quickly, and can capture meaningful data for processes having a characteristic time on the order of milliseconds, tens of milliseconds, hundreds of milliseconds, or longer. Few drugs appear to exert their physiological effects on cells in time periods shorter than this. In one embodiment, the system and method of the present invention may collect and analyze information about the cellular and sub-cellular location of spectroscopic active components, such as drugs and their metabolites. In another embodiment, information can be collected rapidly in a succession of images and these images can be stored and replayed.

The system of the present disclosure may be used to determine a change in a sample over time by analyzing a change in the attribute of the sample in the Raman mode, luminescence mode, absorption mode, bright field modes, crossed polarization modes, birefringence modes, or combinations thereof In another embodiment, the system and method of the present disclosure may also be used to analyze analyte-cell interactions over time by analyzing a change in the attribute of the analyte or the cell in the Raman mode, luminescence mode, absorption mode, bright field modes, crossed polarization modes, birefringence modes, or combinations thereof.

In one exemplary embodiment, the present invention uses a system such as those shown in FIGS. 1 and 2 to detect dynamic changes that occur in sample 100 between a first time interval and a second subsequent time interval using a series of at least first and second sequential chemical images of sample 100. In one embodiment, the system operates in the Raman mode, the luminescence mode or combinations thereof to detect the dynamic changes of the sample. During the first time interval: (i) sample 100 is illuminated with photons from source 110 to thereby produce photons scattered or emitted by sample 100; (ii) first two-dimensional array of detection elements 145 is then used to simultaneously detect scattered or emitted photons in a first predetermined wavelength band (selected by tunable filter 140) from different locations on or within the sample; and (iii) for each of one or more further predetermined wavelength band(s) (each of which is sequentially selected using tunable filter 140), first two-dimensional array of detection elements 145 is thereafter used to simultaneously detect scattered or emitted photons from different locations on or within the sample. The outputs of detector 145 (for each of the wavelengths or wavelength bands selected by tunable filter 140 during the first time interval) are then combined by the processor 150 to generate the first chemical image of the sample.

During the second subsequent time interval: (i) sample 100 is illuminated with photons from source 110 to thereby produce photons scattered or emitted by sample 100; (ii) first two-dimensional array of detection elements 145 is then used to simultaneously detect scattered or emitted photons in a first predetermined wavelength band (selected by tunable filter 140) from different locations on or within the sample; and (iii) for each of one or more further predetermined wavelength band(s) (each of which is sequentially selected using tunable filter 140), first two-dimensional array of detection elements 145 is thereafter used to simultaneously detect scattered or emitted photons from different locations on or within the sample. The outputs of detector 145 (for each of the wavelengths or wavelength bands selected by tunable filter 140 during the first time interval) are then combined by the processor 150 to generate the second chemical image of the sample.

In another embodiment, the system operates in the absorption mode to detect the dynamic changes of the sample. During the first time interval: (i) sample 100 is illuminated with photons from source 101 to thereby produce photons transmitted through sample 100; (ii) first two-dimensional array of detection elements 145 is then used to simultaneously detect photons transmitted through the sample in a first predetermined wavelength band (selected by tunable filter 140); and (iii) for each of one or more further predetermined wavelength band(s) (each of which is sequentially selected using tunable filter 140), first two-dimensional array of detection elements 145 is thereafter used to simultaneously detect photons transmitted through the sample. The outputs of detector 145 (for each of the wavelengths or wavelength bands selected by tunable filter 140 during the first time interval) are then combined by the processor 150 to generate the first chemical image of the sample.

During the second subsequent time interval: (i) sample 100 is illuminated with photons from source 106 to thereby produce photons transmitted through the sample 100; (ii) first two-dimensional array of detection elements 145 is then used to simultaneously photons transmitted through the sample, in a first predetermined wavelength band (selected by tunable filter 140), and (iii) for each of one or more further predetermined wavelength band(s) (each of which is sequentially selected using tunable filter 140), first two-dimensional array of detection elements 145 is thereafter used to simultaneously detect photons transmitted through the sample. The outputs of detector 145 (for each of the wavelengths or wavelength bands selected by tunable filter 140 during the first time interval) are then combined by the processor 150 to generate the second chemical image of the sample.

Operating in the Raman mode, luminescence mode, absorption modes or combinations thereof, dynamic changes occurring in the sample between the first time interval and the second time interval are next detected based on one or more differences between the first and second chemical images. Computer analysis of the chemical image with or without the physical image may be used to detect (or enhance detection of) the dynamic changes. The dynamic changes may also be detected by a user viewing a display of the chemical images.

The present disclosure may be embodied in other specific forms without departing from the spirit or essential attributes of the disclosure. Accordingly, reference should be made to the appended claims, rather than the foregoing specification, as indicated in the scope of the disclosure. Although the foregoing description is directed to the preferred embodiments of the disclosure, it is noted that other variations and modification will be apparent to those skilled in the art, and may be made without departing from the spirit or scope of the disclosure

What is claimed:

1. A system comprising:
   (a) a substantially monochromatic light source that illuminates a sample, along a first optical path, with a plurality of photons to thereby produce, along a second optical path, photons scattered or emitted from different locations on or within the sample wherein the first optical path is at an oblique angle with respect to the second optical path;
   (b) a first white light source located under the sample that illuminates the sample with broadband light to thereby produce, along the second optical path, photons transmitted through the sample; and a second white light source located above the sample that illuminates the sample with broadband light to thereby produce, along the second optical path, photons reflected from different locations on or within the sample;
   (c) at least one processor that generates first control signals that control operation of the substantially monochromatic light source, the first white light source and the second white light source;
   (d) an optical lens, positioned in the second optical path, that collects photons scattered, emitted, or transmitted along the second optical path;
   (e) a two-dimensional tunable filter, responsive to second control signals generated by the at least one processor and positioned in the second optical path, that sequentially passes photons, in each of a plurality of predetermined wavelength bands, which were scattered or emitted from different locations on or within the sample or transmitted through the sample;
   (f) a first two-dimensional array of detection elements, responsive to third control signals generated by the at least one processor, that detects in a spatially accurate manner photons passed by the two-dimensional filter which were scattered or emitted from different locations on or within the sample or transmitted through the sample;
   (g) a second two-dimensional array of detection elements, responsive to fourth control signals generated by the at least one processor, that detects in a spatially accurate manner photons reflected from different locations on or within the sample and generates an image;
   (h) wherein the system includes instructions, executable by the at least one processor, for alternatively configuring the system in a Raman mode, a luminescence mode, an absorption mode and a brightfield transmission or reflection mode:
      (i) wherein, in said Raman mode, the first control signals control operation of the substantially monochromatic light source in order to produce photons scattered from different locations on or within the sample, the second control signals control operation of the two-dimensional tunable filter such that the tunable filter sequentially passes photons, in each of a plurality of predetermined wavelength bands, which were scattered from different locations on or within the sample, and the third control signals control operation of the first two-dimensional array of detection elements in order to detect in a spatially accurate manner photons passed by the two-dimensional filter which were scattered from different locations on or within the sample;
      (ii) wherein, in said luminescence mode, the first control signals control operation of the substantially monochromatic light source in order to produce photons emitted from different locations on or within the sample, the second control signals control operation of the two-dimensional tunable filter such that the tunable filter sequentially passes photons, in each of a plurality of predetermined wavelength bands, which were emitted from different locations on or within the sample, and the third control signals control operation of the first two-dimensional array of detection elements in order to detect in a spatially accurate manner photons passed by the two-dimensional filter which were emitted from different locations on or within the sample;
      (iii) wherein, in said absorption mode, the first control signals control operation of the first white light source in order to produce photons transmitted through the sample, the second control signals control operation of the two-dimensional tunable filter such that the tunable filter sequentially passes photons, in each of a plurality of predetermined wavelength bands, which were transmitted through the sample, and the third control signals control operation of the first two-dimensional array of detection elements in order to detect in a spatially accurate manner photons passed by the two-dimensional filter which were transmitted through the sample;
      (iv) wherein, in said bright field mode, the first control signals control operation of one of the following: the first white light source in order to produce photons transmitted through the sample and the second white light source in order to produce photons reflected from different locations on or within the sample, and the fourth control signals control operation of the second two-dimensional array of detection elements in order to detect in a spatially accurate manner photons which were transmitted or reflected from different locations on or within the sample and to generate a bright field image; and
   (i) wherein the at least one processor combines sequential outputs from the first two-dimensional array of detection elements to generate a chemical image of the sample, wherein each of the sequential outputs from the first two-dimensional array of detection elements corresponds to spatially resolved photons in one of the plurality of predetermined wavelength bands passed by the two-dimensional tunable filter and detected by the first two-dimensional array of detection elements.

2. The system of claim 1, further comprising:
   (j) a first polarizing filter located between the first white light source and the sample; and
   a second polarizing filter located between the sample and the tunable filter, that receives one of transmitted or reflected photons, and is oriented 90 ° with respect to the first polarizing filter,
   (k) wherein the system further includes instructions, executable by the at least one processor, for alternatively configuring the system in a crossed polarization mode:
      (iv) wherein, in said crossed polarization mode, the first control signals control operation of the first white light source in order to produce photons transmitted or reflected from different locations on or within the sample, and the fourth control signals control operation of the second two-dimensional array of detection elements in order to detect in a spatially accurate manner photons which were transmitted or reflected from different locations on or within the sample and to generate a crossed polarization image.

3. The system of claim 2, wherein
(l) the system further includes instructions, executable by the at least one processor, for alternatively configuring the system in a crossed polarization absorption mode:
  (i) wherein, in said crossed polarization absorption mode, the first control signals control operation of the first white light source in order to produce photons transmitted through the sample, the second control signals control operation of the two-dimensional tunable filter such that the tunable filter sequentially passes photons, in each of a plurality of predetermined wavelength bands, which were transmitted from different locations on or within the sample, and the third control signals control operation of the first two-dimensional array of detection elements in order to detect in a spatially accurate manner photons passed by the two-dimensional filter which were transmitted through the sample.

4. The system of claim 2, further comprising a compensator located above the sample,
(l) wherein the system further includes instructions, executable by the at least one processor, for alternatively configuring the system in a birefringence mode:
  (iv) wherein, in said birefringence mode, the first control signals control operation of the first white light source in order to produce photons transmitted from different locations on or within the sample, and the fourth control signals control operation of the second two-dimensional array of detection elements in order to detect in a spatially accurate manner photons which were transmitted from different locations on or within the sample and to generate a birefringence image.

5. In an integrated system that includes one or more light sources, at least one processor, an optical lens, a two-dimensional tunable filter, one or more two-dimensional array of detection elements and instructions, a method comprising,
(a) illuminating a sample, using a substantially monochromatic light source, along a first optical path, with a plurality of photons to thereby produce, along a second optical path, photons scattered or emitted from different locations on or within the sample wherein the first optical path is at an oblique angle with respect to the second optical path;
(b) illuminating the sample using at least one of the following: a first white light source, located under the sample that illuminates the sample with broadband light to thereby produce, along the second optical path, photons transmitted through the sample or a second white light source, located above the sample that illuminates the sample with broadband light to thereby produce, along the second optical path, photons reflected from different locations on or within the sample;
(c) generating, via the at least one processor, first control signals that control operation of the substantially monochromatic light source, the first white light source and the second white light source;
(d) collecting, via the optical lens positioned in the second optical path, ones of photons scattered, emitted or transmitted along the second optical path;
(e) sequentially passing ones of photons, in each of a plurality of predetermined wavelength bands, which were scattered or emitted from different locations on or within the sample or transmitted through the sample, using the two-dimensional tunable filter, responsive to second control signals generated by the at least one processor and positioned in the second optical path;
(f) detecting, in a spatially accurate manner, ones of photons passed by the two-dimensional filter which were scattered or emitted from different locations on or within the sample or transmitted through the sample, using a first two-dimensional array of detection elements, responsive to third control signals generated by the at least one processor;
(g) optionally detecting, in a spatially accurate manner, ones of photons reflected from different locations on or within the sample, using a second two-dimensional array of detection elements, responsive to fourth control signals generated by the at least one processor and generating an image;
(h) executing instructions, by the at least one processor, for alternatively configuring the system in a Raman mode, a luminescence mode, an absorption mode and a brightfield mode:
  (i) wherein, in said Raman mode, the first control signals control operation of the substantially monochromatic light source in order to produce photons scattered from different locations on or within the sample, the second control signals control operation of the two-dimensional tunable filter such that the tunable filter sequentially passes photons, in each of a plurality of predetermined wavelength bands, which were scattered from different locations on or within the sample, and the third control signals control operation of the first two-dimensional array of detection elements in order to detect in a spatially accurate manner photons passed by the two-dimensional filter which were scattered from different locations on or within the sample;
  (ii) wherein, in said luminescence mode, the first control signals control operation of the substantially monochromatic light source in order to produce photons emitted from different locations on or within the sample, the second control signals control operation of the two-dimensional tunable filter such that the tunable filter sequentially passes photons, in each of a plurality of predetermined wavelength bands, which were emitted from different locations on or within the sample, and the third control signals control operation of the first two-dimensional array of detection elements in order to detect in a spatially accurate manner photons passed by the two-dimensional filter which were emitted from different locations on or within the sample;
  (iii) wherein, in said absorption mode, the first control signals control operation of the first white light source in order to produce photons transmitted through the sample, the second control signals control operation of the two-dimensional tunable filter such that the tunable filter sequentially passes photons, in each of a plurality of predetermined wavelength bands, which were transmitted through the sample, and the third control signals control operation of the first two-dimensional array of detection elements in order to detect in a spatially accurate manner photons passed by the two-dimensional filter which were transmitted through the sample;

(iv) wherein, in said bright field mode, the first control signals control operation of one of the following: the first white light source in order to produce photons transmitted through the sample and the second white light source in order to produce photons reflected from different locations on or within the sample, and the fourth control signals control operation of the second two-dimensional array of detection elements in order to detect in a spatially accurate manner photons which were transmitted or reflected from different locations on or within the sample and to generate a bright field image; and (i) combining sequential outputs, via the at least one processor, from the first two-dimensional array of detection elements to generate a chemical image of the sample, wherein each of the sequential outputs from the first two-dimensional array of detection elements corresponds to spatially resolved photons in one of the plurality of predetermined wavelength bands and detected by the first two-dimensional array of detection elements.

6. The method of claim 5, further comprising:

(j) passing the reflected or transmitted photons through a first polarizing filter located between the first white light source and the sample; and passing the reflected or transmitted photons through a second polarizing filter located between the sample and the tunable filter and orientated 90° with respect to the first polarizing filter, (k) executing instructions, by the at least one processor, for alternatively configuring the system in a crossed polarization mode:

wherein the first control signals control operation of the first white light source in order to produce photons transmitted or reflected from different locations on or within the sample, and the fourth control signals control operation of the second two-dimensional array of detection elements in order to detect in a spatially accurate manner photons which were transmitted or reflected from different locations on or within the sample and to generate a crossed polarization image.

7. The system of claim 5, further comprising:

(l) executing instructions, by the at least one processor, for alternatively configuring the system in a crossed polarization absorption mode:

wherein, in said crossed polarization absorption mode, the first control signals control operation of the first white light source in order to produce photons transmitted through the sample, the second control signals control operation of the two-dimensional tunable filter such that the tunable filter sequentially passes photons, in each of a plurality of predetermined wavelength bands, which were transmitted from different locations on or within the sample, and the third control signals control operation of the first two-dimensional array of detection elements in order to detect in a spatially accurate manner photons passed by the two-dimensional filter which were transmitted through the sample.

8. The method of claim 5, further comprising:

(l) passing transmitted photons through a compensator located above the sample;

(m) executing instructions, by the at least one processor, for alternatively configuring the system in a birefringence mode:

wherein, in said birefringence mode, the first control signals control operation of the first white light source in order to produce photons transmitted from different locations on or within the sample, and the fourth control signals control operation of the second two-dimensional array of detection elements in order to detect in a spatially accurate manner photons which were transmitted from different locations on or within the sample and to generate a birefringence image.

9. The method of claim 5 further comprising: analyzing, by the at least one processor, the outputs from one of the following: the first two-dimensional array of detection elements and the second two-dimensional array of detection elements, using one or more aspects of the sample that identify the sample.

10. The method of claim 9, wherein the one or more aspects of the sample comprise wavelength, frequency, phase, polarization, an intensity of wavelength, an intensity of frequency, or combinations thereof.

11. The method of claim 9, further comprising: monitoring a change in the aspect of the sample that identifies the sample.

12. The method of claim 9, wherein the sample comprises a crystalline compound having a plurality of polymorph forms.

13. The method of claim 9, wherein the sample comprises an analyte interacting with a cell.

14. The method of claim 9, wherein the sample comprises a drug.

15. The method of claim 13, wherein the analyte comprises one or more of a drug, a metabolite of the drug, a fluorophore, or combinations thereof.

* * * * *

UNITED STATES PATENT AND TRADEMARK OFFICE
CERTIFICATE OF CORRECTION

PATENT NO. : 7,564,541 B2
APPLICATION NO. : 11/393395
DATED : July 21, 2009
INVENTOR(S) : David Tuschel Page 1 of 1

It is certified that error appears in the above-identified patent and that said Letters Patent is hereby corrected as shown below:

On the Title Page, Item (73) should read
Assignee: ChemImage Corporation, Pittsburgh, PA (US)

Signed and Sealed this
Twenty-sixth Day of July, 2011

David J. Kappos
*Director of the United States Patent and Trademark Office*